United States Patent
Hanna (10) Patent No.: US 6,697,653 B2
(45) Date of Patent: Feb. 24, 2004

(54) REDUCED WIRE COUNT VOLTAGE DROP SENSE

(75) Inventor: D. Alan Hanna, Boulder, CO (US)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 09/975,298

(22) Filed: Oct. 10, 2001

(65) Prior Publication Data

US 2003/0069483 A1 Apr. 10, 2003

(51) Int. Cl.[7] .................................................. A61B 5/00
(52) U.S. Cl. ....................................... 600/310; 600/322
(58) Field of Search ............................... 600/309, 310, 600/322, 323; 607/22

(56) References Cited

U.S. PATENT DOCUMENTS

| | | |
|---|---|---|
| 3,902,806 A | 9/1975 | Bober |
| 4,001,667 A | 1/1977 | Bober |
| 4,730,389 A | 3/1988 | Baudino et al. |
| 4,791,935 A | 12/1988 | Baudino et al. |
| 4,807,629 A | 2/1989 | Baudino et al. |
| 4,813,421 A | 3/1989 | Baudino et al. |
| 5,040,538 A | 8/1991 | Mortazavi |
| 5,267,564 A | 12/1993 | Barcel et al. |
| 5,438,987 A | 8/1995 | Thacker et al. |
| 5,477,853 A * | 12/1995 | Farkas et al. ............... 600/310 |
| 5,634,720 A | 6/1997 | Gallup et al. |
| 5,818,985 A | 10/1998 | Merchant et al. |
| 5,851,178 A | 12/1998 | Aronow |
| 5,891,022 A | 4/1999 | Pologe |
| 5,995,855 A | 11/1999 | Kiani et al. |
| 6,023,541 A | 2/2000 | Merchant et al. |
| 6,026,312 A | 2/2000 | Shemwell et al. |

* cited by examiner

Primary Examiner—Eric F. Winakur
Assistant Examiner—David J. McCrosky
(74) Attorney, Agent, or Firm—Marsh Fischmann & Breyfogle LLP (57) ABSTRACT

The present invention provides a reduced wire count voltage-drop sense system and method wherein the voltage drop across a load device is determinable using only one sense lead regardless of the number of load devices. In one embodiment, the voltage drop across any one of four LEDs (220A–D) in a photoplethysmographic probe when a drive current is applied therethrough via one of four input drive leads (230A–D) connected to separate LED terminals (222A–D) is determinable from a first voltage drop and a second voltage drop, for example, by subtracting the second voltage drop, or a portion thereof, from the first voltage drop. The first voltage drop is measurable across a terminal (232A–D) of the input drive lead (230A–D) connected to the LED (220A–D) across which the voltage drop is to be determined and a terminal (252) of a sense lead (250) connected to a common LED terminal (224). The second voltage drop is measurable across the sense lead terminal (252) and a terminal (242) of a common drive lead (240) connected to the common LED terminal (224).

34 Claims, 4 Drawing Sheets

REDUCED WIRE COUNT VOLTAGE DROP SENSE

FIELD OF THE INVENTION

The present invention relates generally to the determination of a voltage drop across a load device, and more particularly to the determination of the voltage drop across any one of a plurality of load devices using sense leads. The present invention has particular application to the determination of the voltage drops across light signal emitters within a photoplethysmographic probe.

BACKGROUND OF THE INVENTION

In photoplethysmography, light signals are transmitted through a tissue under test to non-invasively determine the level of one or more blood analytes such as oxyhemoglobin (O2Hb), deoxyhemoglobin or reduced hemoglobin (RHb), carboxyhemoglobin (COHb) or methemoglobin (MetHb). One type of photophlethysmographic device includes a probe having four light signal emitters and one detector. The probe is attachable to a patient's appendage (e.g. finger, ear lobe, nasal septum, foot) and is connectable via a cable with a monitor unit. The light signal emitters may comprise, for example, light-emitting-diodes (LEDs) or laser diodes, that are operable to transmit light signals characterized by distinct center wavelengths $\lambda_1 \neq \lambda_2 \neq \lambda_3 \neq \lambda_4$ through the patient's appendage to the detector. The monitor unit supplies drive signals via drive leads in the probe cable to the light signal emitters for turning the light signal emitters on and off as desired. The monitor unit also receives an output signal via an output lead in the cable from the detector indicative of the intensities of the transmitted light signals (light exiting the patient's appendage is referred to as transmitted). The monitor processes the output signal from the detector and, since different analytes have unique light absorbency characteristics, determines the concentrations of various blood analytes in the patient's blood based on the intensities of the transmitted light signals. See, e.g., U.S. Pat. No. 5,842,979.

The center wavelength of the light signal output by each light signal emitter may be dependent upon a number of factors, including the operating temperature of the emitter. As may be appreciated, the accuracy of the determination of the concentrations of various blood analytes may be improved if wavelength changes in the light signals output by the emitters are tracked and compensated for in the determination of blood analyte concentrations. One manner of tracking the wavelength changes is to monitor changes in the voltage drops across the junction of the light signal emitters. Sensitive measurement techniques must be employed to monitor the voltage drop changes across the light signal emitters since such changes are typically in the range of only 10 to 30 millivolts, whereas the voltage drops in the entire light signal emitter circuit are much higher.

SUMMARY OF THE INVENTION

The present invention provides a reduced wire count voltage-drop sense system and method wherein the voltage drop across a load device is determinable using only one sense lead regardless of the number of load devices. By permitting the voltage drop to be determined using only one sense lead, the reduced wire count voltage-drop sense system and method of the present invention achieves an advantage over a dual sense wire scheme that employs a common sense lead and at least one sense lead for each load device.

The reduced wire count voltage-drop sense system and method of the present invention has particular applicability to the field of photoplethysmography wherein it is desirable to determine the voltage drops across one or more light signal emitters operable to illuminate a patient tissue site for determination of one or more blood analyte levels. By reducing the number of sense leads required, the component cost and manufacturing complexity of a photoplethysmographic probe are reduced thereby reducing overall probe cost. Reducing the number of sense leads can also beneficially improve the reliability of the photoplethysmographic probe. Although various aspects and advantages of the present invention are illustrated in the context of photoplethysmography, it will be appreciated that the system and method of the present invention may have applicability in other fields.

According to one aspect of the present invention, a reduced wire count voltage-drop sense system for use in photoplethysmography includes an input drive lead, a return drive lead and a single sense lead. The input drive lead extends between an associated input drive lead terminal and an associated light signal emitter input terminal. The return drive lead extends between a light signal emitter output terminal and a return drive lead terminal. The sense lead extends between the light signal emitter output terminal and a sense lead terminal. The voltage drop across a light signal emitter (e.g., an LED or a laser diode) connected between the light signal emitter input terminal and the light signal emitter output terminal when a drive current is applied therethrough via the input drive lead is determinable from a first voltage drop, measurable across the input drive lead terminal and the sense lead terminal, and a second voltage drop, measurable across the sense lead terminal and the return drive lead terminal. In this regard, the voltage drop across the light signal emitter is, for example, determinable by subtracting the second voltage drop from the first voltage drop.

The sense system of the present invention provides for the accurate determination of the voltage drop across the light signal emitter using only one sense lead as opposed to two sense leads in a dual sense wire scheme by recognizing that the input drive lead and the return drive may be configured to have substantially similar resistance values. In this regard, the input drive lead and the return drive lead may comprise substantially equal length wires made of the same material and having substantially equal diameters. Further, the wires comprising the input drive lead and the return drive lead may be disposed within the same sheath so that they have substantially similar temperature profiles along their length.

According to another aspect of the present invention, a reduced wire count voltage-drop sense system for use in photoplethysmography includes a plurality of input drive leads, a common return lead, and a single sense lead. Each of the input drive leads extends between a separate input drive lead terminal associated with the input drive lead and a light signal emitter input terminal associated with the input drive lead. The common return lead extends between a common light signal emitter output terminal and a common return lead terminal. The sense lead extends between the common light signal emitter output terminal and the sense lead terminal. A voltage drop across any one of a plurality of light signal emitters (e.g., an LED or a laser diode) operable to illuminate a patient tissue site and connected between separate light signal emitter input terminals and the common light signal emitter output terminal when a drive current is applied therethrough via an associated one of the input drive leads is determinable from a first voltage drop and a second voltage drop. The first voltage drop is measurable across the input drive lead terminal associated with the input drive lead associated with the light signal emitter across which the voltage drop is to be determined and the sense lead terminal. The second voltage drop is measurable across the sense lead terminal and the common return lead terminal.

When only one drive current is applied to the light signal emitters at a time, the voltage drop across such light signal emitter is, for example, determinable by subtracting the second voltage drop from the first voltage drop since the second voltage drop results only from the drive current applied through such load device. When more than one drive current is simultaneously applied through more than one of the light signal emitters, the second voltage drop results from all of the drive currents that are applied through the light signal emitters and not just the drive current through the light signal emitter across which the voltage drop is desired. In this regard, the desired voltage drop is, for example, determinable by subtracting a portion of the second voltage drop from the first voltage drop. The portion of the second voltage drop that is subtracted from the first voltage drop may be obtained in accordance with the level of the drive current applied through the light signal emitter across which the voltage drop is desired in comparison to the other drive currents. For example, if there are four equal level drive currents simultaneously applied to four light signal emitters, then one-fourth of the second voltage drop may be subtracted from the first voltage drop.

It will be appreciated that the common return lead may carry, on average, more current than any one of the individual drive leads because it serves as the common return for all of the drive currents. This may affect the temperature, and thus the resistance, of the common return lead. In this regard, in addition to configuring the input drive leads and the common return lead as substantially equal length wires of the same material within the same sheath, the common return lead may be provided with a larger cross-sectional area along its length. For example, the cross-sectional area of the wire comprising the common return lead may equal the number of input drive leads multiplied by the cross-sectional area of the wires comprising the input drive leads. It will be appreciated that when the common return lead wire has a larger diameter, it may be desirable to scale the second voltage drop accordingly before subtracting it from the first voltage drop. For example, if the common return lead has four times the cross-sectional area than each of the input drive leads, then the second voltage drop may be multiplied by a factor of four.

According to one more aspect of the present invention, a reduced wire count photoplethysmographic probe includes a plurality of light signal emitters (e.g., LEDs or laser diodes), a plurality of input drive leads, a common return drive lead, and a single sense lead. Each light signal emitter includes an input terminal and an output terminal single. The output terminals of the light signal emitters are connected in common with one another. Each input drive lead is associated with one of the light signal emitters and extends between an associated input drive lead terminal and the input terminal of its associated light signal emitter. The common return drive lead extends between the commonly connected output terminals of the light signal emitters and a common return drive lead terminal. The sense lead extends between the commonly connected output terminals of the light signal emitters and the sense lead terminal. A voltage drop across any one of the light signal emitters when it is turned on by applying a drive current therethrough via the input drive lead associated therewith is determinable from a first voltage drop and a second voltage drop. The first voltage drop is measurable across the input drive lead terminal associated with the input drive lead associated with the light signal emitter across which the voltage drop is to be determined and the sense lead terminal. The second voltage drop is measurable across the sense lead terminal and the common return drive lead terminal.

According to a further aspect of the present invention, a reduced wire count photoplethysmographic probe includes at least two pairs of light signal emitters (e.g., LEDs or laser diodes), a plurality of input drive leads, a common return drive lead, and a single sense lead. The light signal emitters in each a pair of light signal emitters are connected in a back-to-back relation with one another between an input terminal of the pair and an output terminal of the pair. The lights signal emitters in each pair are oriented such that one of the light signal emitters is forward biased and one is reverse biased when a voltage is applied across the input and output terminals of the pair. The output terminals of each pair of light signal emitters is connected in common with one another. Each input drive lead is associated with one of the pairs of light signal emitters and extends between an associated input drive lead terminal and the input terminal of its associated pair of light signal emitters. The common return drive lead extends between the commonly connected output terminals of the pairs of light signal emitters and a common return drive lead terminal. The sense lead extends between the commonly connected output terminals of the pairs of light signal emitters and a sense lead terminal. The voltage drop across any one of the pairs of light signal emitters, and hence either one of the light signal emitters in the pair, when a drive current is applied therethrough via the input drive lead associated therewith is determinable from a first voltage drop and a second voltage drop. The first voltage drop is measurable across the input drive lead terminal associated with the input drive lead associated with the pair of light signal emitters across which the voltage drop is desired and the sense lead terminal. The second voltage drop is measurable across the sense lead terminal and the common return drive lead terminal.

According to yet another aspect of the present invention, a method of determining a desired voltage drop across any one of a plurality of light signal emitters operable to illuminate a patient tissue site and having separate input terminals and commonly connected output terminals proceeds in the following manner. A first voltage drop is measured across a sense lead terminal connected by a sense lead to the commonly connected output terminals of the light signal emitters and an input drive lead terminal connected by an input drive lead to the input terminal of the light signal emitter across which the desired voltage drop is to be determined when a drive current is supplied thereto via the input drive lead. A second voltage drop is measured across the same sense lead terminal and a common return drive lead terminal connected by a common return drive lead to the commonly connected output terminals of the light signal emitters. The desired voltage drop is then determined utilizing the first voltage drop and the second voltage drop. It will be appreciated that the method of the present invention does not employ the direct measurement of the voltage drop across a pair of sense lead terminals connected by dual sense leads to the input terminal of the light signal emitter across which the voltage drop is desired and the commonly connected output terminals of the light signal emitters.

When only one drive current is applied at a time, the desired voltage drop may, for example, be determined by subtracting the second voltage drop from the first voltage drop. When multiple drive currents are simultaneously supplied to more than one of the plurality of light signal emitters, the desired voltage drop may, for example, be determined by subtracting a portion of the second voltage drop from the first voltage drop. In this regard, the second voltage drop may be apportioned in accordance with the level of each drive current that is supplied to the light signal emitters in order to obtain the portion of the second voltage drop that is subtracted from the first voltage drop. Further, when the common return drive lead has a different cross-sectional area than the input drive lead, the second voltage drop may be multiplied by the ratio of the cross-sectional area of the common return drive lead to the cross-sectional area of the input drive lead prior to subtracting the second voltage drop from the first voltage drop.

These and other aspects and advantages of the present invention will be apparent upon review of the following Detailed Description when taken in conjunction with the accompanying figures.

DESCRIPTION OF THE DRAWINGS

For a more complete understanding of the present invention and further advantages thereof, reference is now made to the following Detailed Description, taken in conjunction with the figures, in which.

DETAILED DESCRIPTION

Figure 1:
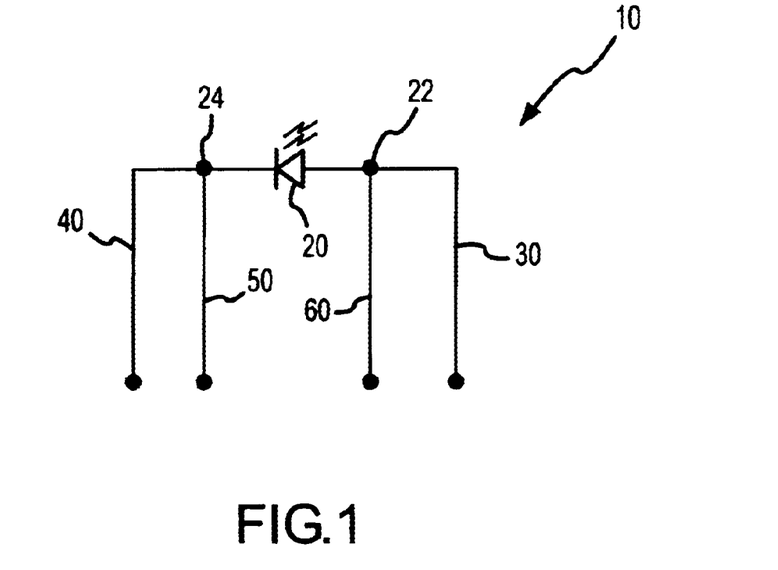
FIG. 1 is a schematic diagram of a dual sense wire voltage drop sense system implementable in a single LED photoplethysmographic probe.

Referring to FIG. 1, a schematic diagram of a dual sense wire scheme for monitoring the voltage drop across a single LED 20 in a photoplethysmographic probe is shown. The LED 20 is driven by a drive current supplied through a drive circuit comprising a pair of drive leads 30, 40 connected to opposing input and output terminals 22, 24 of the LED. The dual sense wire scheme 10 utilizes two separate sense leads 50, 60, one being connected to the input terminal 22 and one to the output terminal 24 of the LED 20. The voltage drop across the LED 20 is directly ascertainable by measuring the voltage drop across the pair of sense leads 50, 60. It will be appreciated that the dual sense wire scheme of FIG. 1 requires two sense wires 50 in addition to the two drive leads 30, 40.

Figure 2:
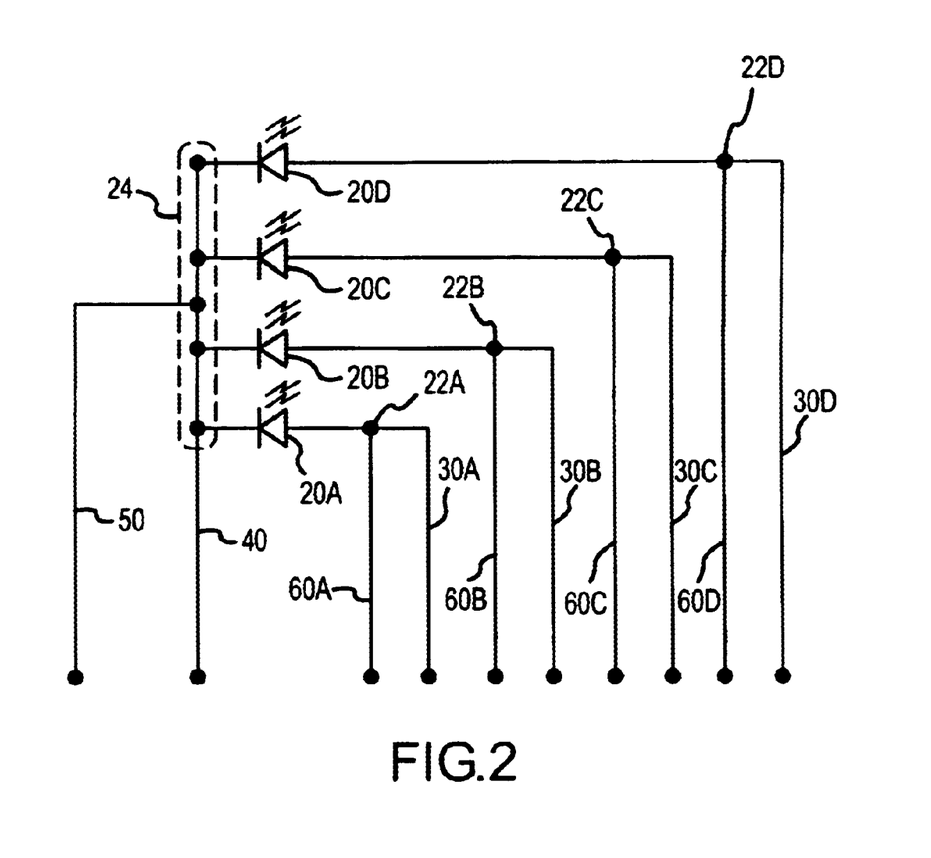
FIG. 2 is a schematic diagram of the dual sense wire voltage drop sense system implementable in a photoplethysmographic probe having four LEDs.

As is shown in FIG. 2, the dual sense wire scheme shown in FIG. 1 may be extended to four LEDs 20A–D in a photoplethysmographic probe. The four LEDs 20A–D are driven by separate drive currents supplied thereto by a drive circuit comprising separate drive leads 30A–D connected to separate input terminals 22A–D of the LEDs 20A–D and a common drive lead 40 connected to a common terminal 24 of the LEDs 20A–D. A common sense lead 50 is connected to the common terminal 24 of the LEDs 20A–D and sense leads 60A–D associated with each of the LEDs 20A–D are separately connected to the input terminal 22A–D of its associated LED 20A–D. The voltage drop across any one of the LEDs 20A–D may be directly measured across the common sense lead 50 and the sense lead 60A–D associated with such LED 20A–D. It will be appreciated that implementation of the sense wire scheme shown in FIG. 2 in a photoplethysmographic probe requires a total of ten wires in the cable sheath of the photoplethysmographic probe.

Figure 3:
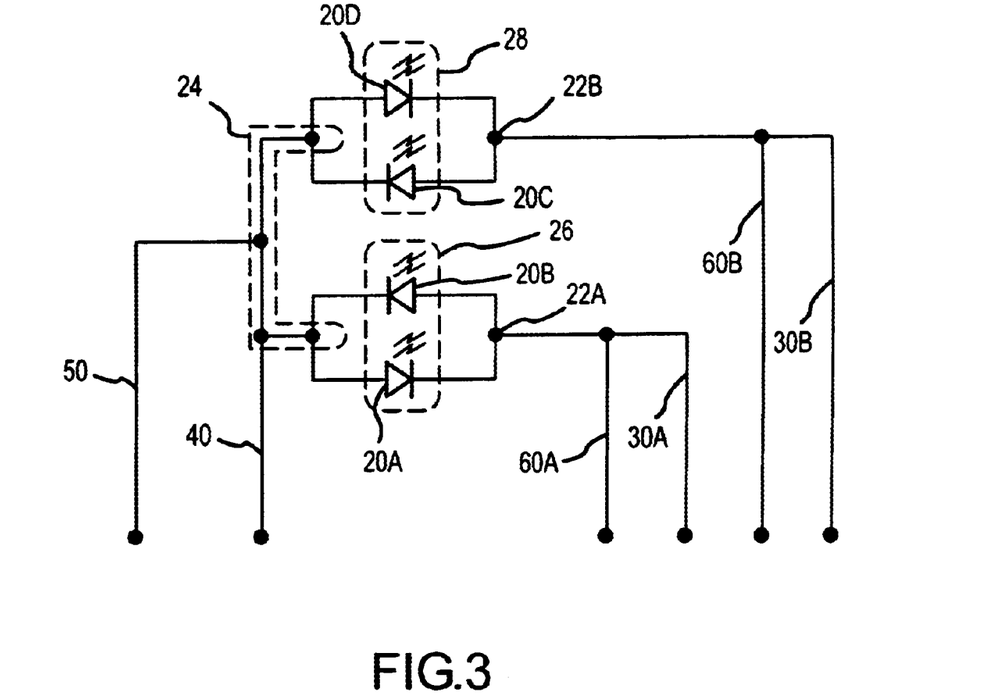
FIG. 3 is a schematic diagram of the dual sense wire voltage drop sense system implementable in a photoplethysmographic probe having two pairs of LEDs arranged in a back-to-back configuration.

As is shown in FIG. 3, the dual sense wire scheme shown in FIG. 1 may be extended to four LEDs 20A–D connected in a back-to-back configuration in a photoplethysmographic probe. In the back-to-back configuration, two of the LEDs 20A–B are grouped in a first pair 26 and two of the LEDs 20C–D are grouped in a second pair 28. In each pair 26, 28, the LEDs 20A–B, 20C–D are connected in parallel with one another and oriented in opposing directions so that one of the LEDs 20A, 20C is forward biased and the other LED 20B, 20D is reverse biased when a voltage difference is applied across each pair 26, 28 of LEDs 20A–B, 20C–D. Each pair 26, 28 of LEDs 20A–B, 20C–D are driven by drive currents supplied thereto through a drive circuit comprising separate drive leads 30A–B connected to one side of each pair 26, 28 of LEDs 20A–B, 20C–D (the input terminals 22A–B) and a common lead 40 connected to the opposite side of both pairs 26, 28 of LEDs 20A–B, 20C–D (the common terminal 24). A common sense lead 50 is connected to the common terminal 24 of the pairs 26, 28 of the LEDs 20A–B, 20C–D and separate sense leads 60A–B associated with each pair 26, 28 of LEDs 20A–B, 20C–D are separately connected to the input terminals 22A–B of each associated pair 26, 28 of LEDs 20A–B, 20C–D. The voltage drop across either one of the pairs 26, 28 of LEDs 20A–B, 20C–D (and hence either one of the LEDs 20A–B, 20C–D in a pair 26, 28) may be directly measured across the common sense lead 50 and the sense lead 60A–B associated with such pair 26, 28 of LEDs 20A–B, 20C–D. It will be appreciated that implementation of the sense wire scheme shown in FIG. 3 in a photoplethysmographic probe requires a total of six wires in the cable sheath of the photoplethysmographic probe.

Figure 4:
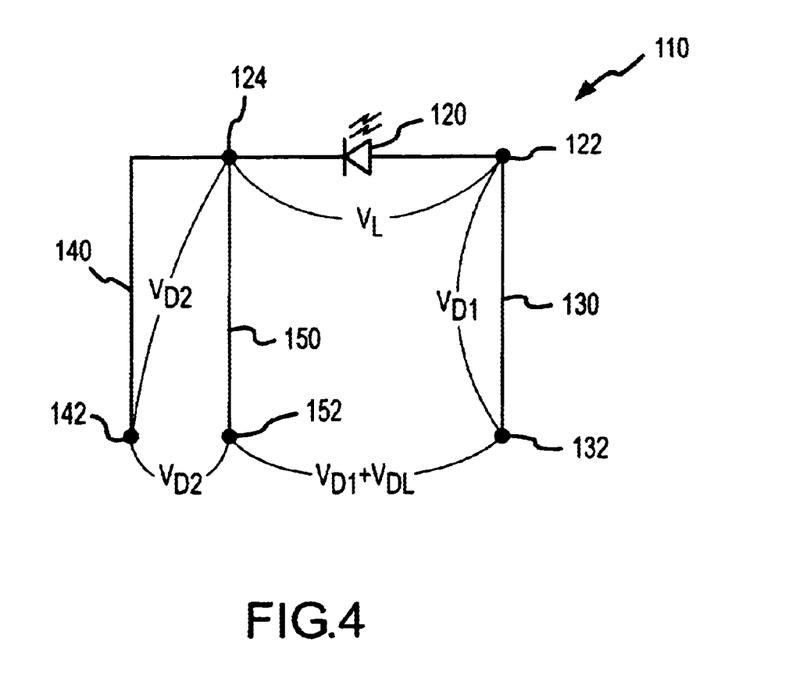
FIG. 4 is a schematic diagram of a reduced wire count voltage drop sense system implementable in a single LED photoplethysmographic probe in accordance with the present invention.

Referring now to FIG. 4 there is a shown a schematic diagram of a reduced wire count voltage drop sense system 110 in accordance with the present invention. The sense system 110 is for determining the voltage drop across a load device when a current is applied through the load device. As is shown, the load device may be an LED 120. In this regard, the sense system 110 is particularly suited for implementation within a photophlethysmographic probe wherein it is desirable to determine the voltage drop across the LED 120 within the probe in order to make an assessment regarding shifting of the center wavelength of the light output by the LED 120 due, for example, to temperature variations.

The sense system 110 includes a first drive lead 130, a second drive lead 140, and a sense lead 150. The first drive lead 130 extends from a first lead terminal 132 to a first LED connection terminal 122. The second drive lead 140 extends from a second LED connection terminal 124 to a second lead terminal 142. The sense lead 150 extends from the second LED connection terminal 124 to a sense terminal 152.

A drive current for driving operation of the LED 120 (i.e., for causing the LED 120 to emit a light signal) may flow from the first lead terminal 132 through the first drive lead 130, the LED 120, and the second drive lead 140 to the second lead terminal 142. It will be appreciated that associated with the drive current through the LED 120 there is a voltage drop $V_L$. There is also a voltage drop $V_{D1}$ in the first drive lead 130, as well as a voltage drop $V_{D2}$ in the second drive lead 140.

Using the sense system 110, the voltage drop $V_L$ across the LED 120 is determinable in the following manner. Since no current flows through the sense lead 150, the sense terminal 152 is at the same potential as the second LED connection terminal 124. Thus, the voltage drop $V_{D1}$ in the first drive lead 130 plus the voltage drop $V_L$ in the LED 120 (i.e., $V_{D1}+V_L$) may be measured between the first lead terminal 132 and the sense terminal 152. The voltage drop $V_{D2}$ in the second drive lead 140 may be measured across the sense terminal 152 and the second lead terminal 142. Assuming that the resistances of the first and second drive leads 130, 140 are substantially equal to one another, one may derive the following approximate expression for the voltage drop $V_L$ in the LED 120 when it is operating:

$$V_L \approx (V_{D1}+V_L) - V_{D2} \qquad (1)$$

The accuracy of the approximate expression for $V_L$ depends upon how close the resistances in the first and second drive leads 130, 140 are to one another. The assumption that their resistances are substantially equal to one another is reliable since, among other factors, the first and second drive leads 130, 140 may be comprised of the same length and diameter wire, they may be comprised of the same material, they may be housed in the same sheath so that the leads 130, 140 have the same temperatures along their lengths, and they both have the same current load therethrough.

Figure 5:
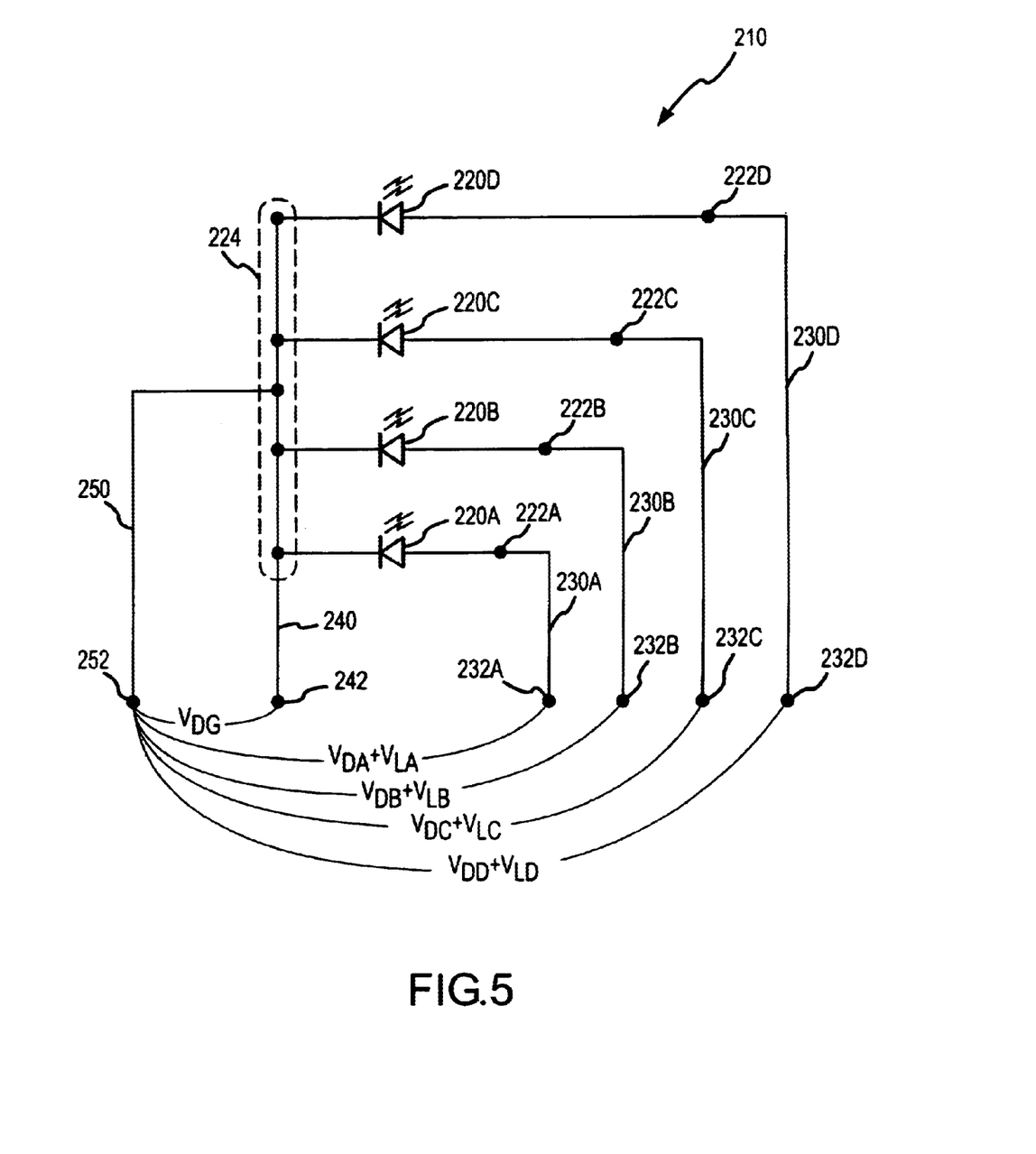
FIG. 5 is a schematic diagram of a reduced wire count voltage drop sense system implementable in a photoplethysmographic probe having four LEDs in accordance with the present invention.

Referring now to FIG. 5 there is shown a schematic diagram illustrating one manner of extending the concepts of the reduced wire count voltage drop sense system of FIG. 4 to multiple load devices. FIG. 5 illustrates a reduced wire count voltage drop sense system 210 for determining the voltage drops across four load devices. In the illustrated embodiment, the load devices comprise LEDs 220A–D within a photophlethysmographic probe designed to transmit four light signals. Each LED 220A–D is connected between a separate LED connection terminal 222A–D corresponding to such LED 220A–D and an LED connection terminal common to all four LEDs 220A–D (the common LED connection terminal 224). Four separate drive leads 230A–D corresponding with the four LEDs 220A–D extend between associated drive lead terminals 232A–D and the separate LED connection terminals 222A–D associated with each of the LEDs 220A–D. A common drive lead 240 extends between the common LED connection terminal 224 and a common drive terminal 242. A sense lead 250 connects the common LED connection terminal 224 with a sense terminal 252. It will be appreciated that the sense system 210 of FIG. 5 includes only six leads, a substantial reduction in comparison to the ten leads in the dual sense wire arrangement for obtaining the voltage drop across four LEDs such as illustrated in FIG. 2.

Drive currents for driving operation of each LED 220A–D may flow from each of the drive lead terminals 232A–D through the drive leads 230A–D, the LEDs 220A–D, and the common lead 240 to the common drive terminal 242. The drive currents may be configured to provide for multiplexing of the operation of the separate LEDs 220. For example, the drive currents may be configured to provide for time-division multiplexing of the LEDs 220A–D. Associated with each drive current there are corresponding voltage drops $V_{LA}$, $V_{LB}$, $V_{LC}$, $V_{LD}$ in the LEDs 220A–D and corresponding voltage drops $V_{DA}$, $V_{DB}$, $V_{DC}$, $V_{DD}$ in the separate drive leads 230A–D. There is also a voltage drop $V_{DG}$ in the common drive lead 240. It will be appreciated that the voltage drop $V_{DG}$ in the common drive lead 240 is dependent upon the number of drive currents that are flowing during a given time period. For example, if all four drive currents are flowing simultaneously during a given time period then the voltage drop $V_{DG}$ in the common lead 240 corresponds to all four drive currents. Likewise, if only one of the drive currents is flowing during a given time period then the voltage drop $V_{DG}$ in the common lead 240 corresponds to only that drive current.

When only one drive current is on during a given time period, determining the voltage drop across each LED 220A–D proceeds in a manner similar to that of the embodiment shown in FIG. 4. For example, to determine the voltage drop $V_{LA}$ across LED 220A while its drive current is on, the voltage drop $V_{DG}$ in the common lead 240 measured across the sense terminal 252 and the common terminal 242 is subtracted from the sum of the voltage drops in LED 220A and drive lead 230A (i.e., $V_{DA}+V_{LA}$) measured across drive lead terminal 232A and sense terminal 252. The voltages drops $V_{LB}$, $V_{LC}$, $V_{LD}$ in the other LEDs 220B–D are determinable in a similar manner when their corresponding drive currents are on.

It is also possible to determine the voltage drops $V_{LA}$, $V_{LB}$, $V_{LC}$, $V_{LD}$ in the LEDs 220A–D when more than one drive current is on during a given time period. In this regard, when multiple drive currents are on during a given time period, then the voltage drop $V_{DG}$ in the common lead 240 measured across the sense terminal 252 and the common terminal 242 may be apportioned in accordance with the level of each drive current that is on. For example, if four drive currents of equal level are on then $V_{DG}$ may be divided by four and each fourth subtracted from the measured voltage drop across its corresponding drive lead terminal 232A–D and the sense terminal 252 to obtain the voltage drops $V_{LA}$, $V_{LB}$, $V_{LC}$, $V_{LD}$ in the LEDs 220A–D. In this regard, the following approximation may be used:

$$V_{Li} \approx (V_{Di} + V_{Li}) - \frac{1}{4} V_{DG}, \; i = A, B, C, D \qquad (2)$$

By way of another example, if the drive current through LED 220A is twice as large as the drive currents through the other LEDs 220B–C, then two-fifths of $V_{DG}$ as measured across the sense terminal 252 and the common terminal 242 may be subtracted from the sum $V_{LA}+V_{DA}$ as measured across drive terminal 232A and the sense terminal 252 to obtain voltage drop $V_{LA}$ in LED 220A and one-fifth of $V_{DG}$ as measured across the sense terminal 252 and the common terminal 242 may be subtracted from the sums $V_{LB}+V_{DB}$, $V_{LC}+V_{DC}$, and $V_{LD}+V_{DD}$ as measured across drive terminals 232B–C and the sense terminal 252 to obtain voltage drops $V_{LB}$, $V_{LC}$, $V_{LD}$ in LEDs 220B–C. In this regard, the following approximations may be used:

$$V_{LA} \approx (V_{DA} + V_{LA}) - \frac{2}{5} V_{DG} \qquad (3)$$

-continued $$V_{Li} \approx (V_{Di} + V_{Li}) - \frac{1}{5}V_{DG}, \; i = B, C, D \quad (4)$$

As may be appreciated, in deriving the approximations set forth in equations (2), (3) and (4), it was assumed that the resistance of the common drive lead 240 is the same as the resistance of each of the four individual drive leads 230A–D. However, in the sense system 210 of FIG. 5, the common drive lead 240 carries, on average, four times the current that each of the individual drive leads 230A–D carries on average (assuming equal level drive currents in each drive lead 230A–D). This may result in the common drive lead 240 running hotter than the separate drive leads 230A–D, unbalancing temperature and giving the common drive lead 240 a different resistance than that of the individual drive leads 230A–D. This can be compensated for by providing a common drive lead 240 having four times the cross-sectional area of one of the individual drive leads 230A–D. This provides for an average heat generation per unit length that is the same for the common drive lead 240 and each of the individual drive leads 230A–D. To compensate for the lower resistance of the larger cross-sectional area common drive lead 240, $V_{DG}$ as measured across the sense terminal 252 and the common terminal 242 may be multiplied by a factor of four before it is subtracted from the sum of the voltage drops in LEDs 220A–D and drive leads 230A–D measured across the drive lead terminals 232A–D and the sense terminal 252. In this regard, the approximation of equation (2) becomes:

$$V_{Li} \approx (V_{Di}+V_{Li})-V_{DG}, \; i=A,B,C,D \quad (5)$$

and the approximations of equations (3) and (4) become:

$$V_{LA} \approx (V_{DA} + V_{LA}) - \frac{8}{5}V_{DG} \quad (6)$$

$$V_{Li} \approx (V_{Di} + V_{Li}) - \frac{4}{5}V_{DG}, \; i = B, C, D \quad (7)$$

Figure 6:
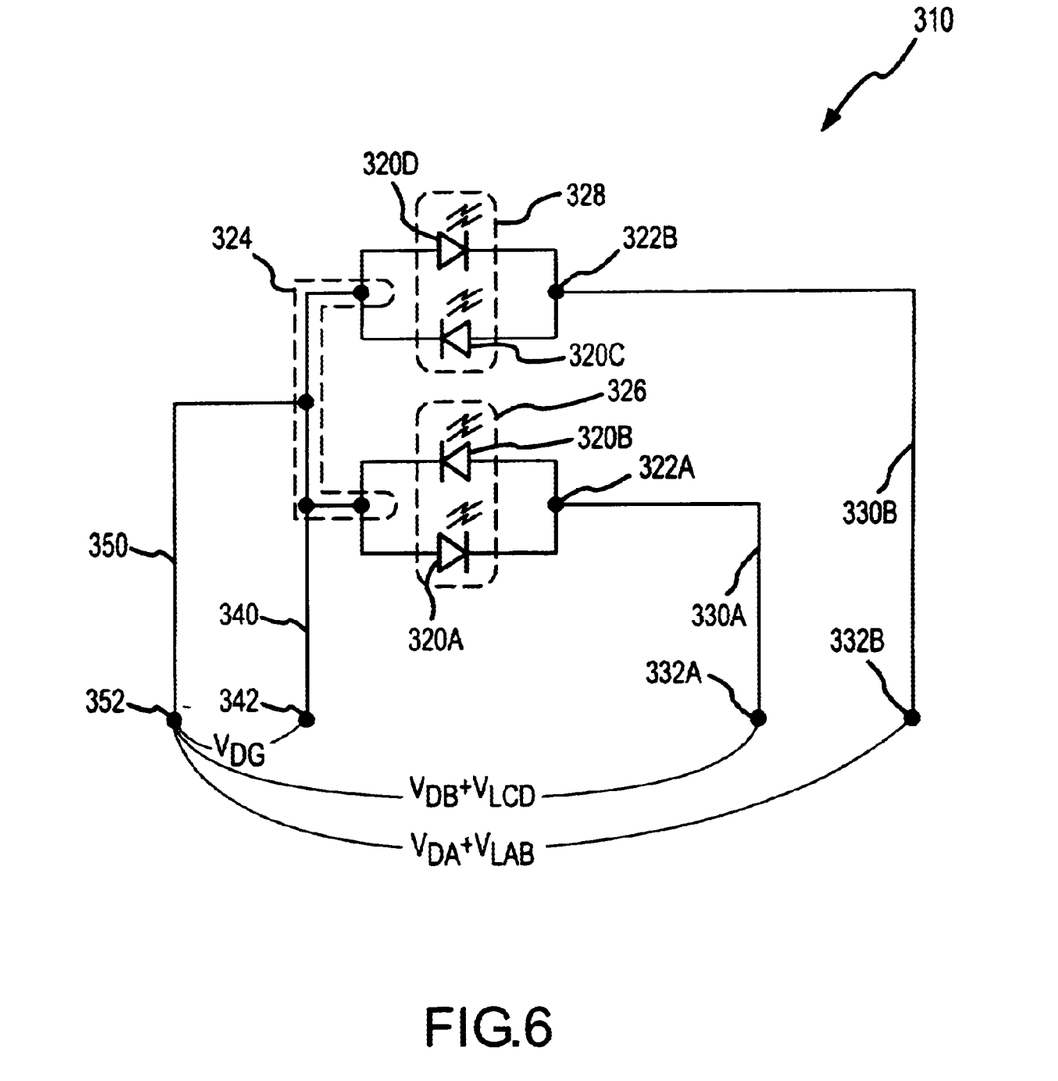
FIG. 6 is a schematic diagram of a reduced wire count voltage drop sense system implementable in a photoplethysmographic probe having two pairs of LEDs arranged in a back-to-back configuration in accordance with the present invention.

Referring now to FIG. 6 there is shown a schematic diagram illustrating one manner of extending the concepts of the reduced wire count voltage drop sense system of FIG. 3 to multiple load devices connected in pairs of back-to-back devices. FIG. 6 illustrates a reduced wire count voltage drop sense system 310 for determining the voltage drops across any one of four load devices connected in two pairs of back-to-back devices. In the illustrated embodiment, the load devices comprise LEDs 320A–D within a photophlethysmographic probe designed to transmit four light signals. Two of the LEDs 320A–B are grouped in a first pair 326 and two of the LEDs 320C–D are grouped in a second pair 328. The LEDs 320A–B, 320C–D of each pair 326, 328 are connected in parallel with one another and oriented in opposing directions so that one of the LEDs 320A, 320C of each pair 326, 328 is forward biased and the other LED 320B, 320D of each pair 326, 328 is reverse biased when a voltage difference is applied across the pairs 326, 328 of LEDs 320A–B, 320C–D. Each pair 326, 328 of LEDs 320A–B, 320C–D is connected between a separate LED connection terminal 322A–B corresponding to such pair 326, 328 and an LED connection terminal common to both pairs 326, 328 (the common LED connection terminal 324). Two separate drive leads 330A–B corresponding with the two pairs 326, 328 of LEDs 320A–B, 320C–D extend between associated drive lead terminals 332A–B and the LED connection terminals 322A–B associated with each pair 326, 328. A common drive lead 340 extends between the common LED connection terminal 324 and a common drive terminal 342. A sense lead 350 connects the common LED connection terminal 324 with a sense terminal 352. It will be appreciated that the sense system 310 of FIG. 6 includes only four leads, a substantial reduction in comparison to the six leads in the dual sense wire arrangement for obtaining the voltage drop across four back-to-back configured LEDs such as illustrated in FIG. 3.

When only one drive current is on during a given time period, determining the voltage drop $V_{LAB}$, $V_{LCD}$ across any of the pairs 326, 328, and hence the voltage drop across each parallel LED 330A–B, 330C–D of the pairs 326, 328 proceeds in a manner similar to that of the embodiment shown in FIG. 4. For example, to determine the voltage drop $V_{LAB}$ across the first pair 326 of LEDs 320A–B while their drive current is on, the voltage drop $V_{DG}$ in the common lead 340 measured across the sense terminal 352 and the common terminal 342 is subtracted from the sum of the voltage drops in the first pair 326 of LEDs 320A–B and drive lead 330A (i.e., $V_{DA}+V_{LAB}$) measured across drive lead terminal 332A and sense terminal 352. The voltages drop $V_{LCD}$ in the other pair of LEDs 330C–D is determinable in a similar manner when its corresponding drive current is on.

When more than one drive current is on during a given time period, the voltage drops $V_{LAB}$, $V_{LCD}$ in either pair 326, 328 of LEDs 320A–B, 320C–D, and hence across any of the LEDs 320A–B, 320C–D of a pair 326, 328, may be determined in similar manner as with the embodiment shown in FIG. 5. In this regard, when multiple drive currents are on during a given time period, then the voltage drop $V_{DG}$ in the common lead 340 measured across the sense terminal 352 and the common terminal 342 may be apportioned in accordance with the level of each drive current that is on. For example, if two drive currents of equal level are on then $V_{DG}$ may be divided by two and each half subtracted from the measured voltage drop across its corresponding drive lead terminal 332A–B and the sense terminal 352 to obtain the voltage drops $V_{LAB}$, $V_{LCD}$ in each pair 326, 328. In this regard, the following approximations may be used:

$$V_{LAB} \approx (V_{DA} + V_{LAB}) - \frac{1}{2}V_{DG} \quad (8)$$

$$V_{LCD} \approx (V_{DB} + V_{LCD}) - \frac{1}{2}V_{DG} \quad (9)$$

As with the embodiment shown in FIG. 5, the common drive lead 340 carries, on average, twice as much current (assuming equal level drive currents in both drive leads 330A–B), and this may result in the common drive lead 340 running hotter than the separate drive leads 330A–B, unbalancing temperature and giving the common drive lead 340 a different resistance than that of the individual drive leads 330A–B. By providing a common drive lead 340 having twice the cross-sectional area of one of the individual drive leads 330A–B, an average heat generation per unit length that is the same for the common drive lead 340 and each of the individual drive leads 330A–B may be achieved. To compensate for the lower resistance of the larger cross-sectional area common drive lead 340, $V_{DG}$ as measured across the sense terminal 352 and the common terminal 342 may be multiplied by a factor of two before it is subtracted from the sum of the voltage drops in each pair 326, 328 of LEDs 320A–B, 320C–D and drive leads 330A–B measured across the drive lead terminals 332A–B and the sense terminal 352. In this regard, the approximation of equations (8) and (9) become:

$$V_{LAB} \approx (V_{DA} + V_{LAB}) - V_{DG} \quad (10)$$

$$V_{LCD} \approx (V_{DB} + V_{LCD}) - V_{DG} \quad (11)$$

While various embodiments of the present invention have been described in detail, further modifications and adaptations of the invention may occur to those skilled in the art. However, it is to be expressly understood that such modifications and adaptations are within the spirit and scope of the present invention.

What is claimed is:

1. A reduced wire count voltage-drop sense system for use in photoplethysmography comprising:
   an input drive lead extending between an associated input drive lead terminal and an associated light signal emitter input terminal;
   a return drive lead extending between a light signal emitter output terminal and a return drive lead terminal; and
   a sense lead extending between said light signal emitter output terminal and a sense lead terminal;
   wherein a voltage drop across a light signal emitter operable to illuminate a patient tissue site and connected between the light signal emitter input terminal and the light signal emitter output terminal when a drive current is applied therethrough via said input drive lead is determinable from a first voltage drop and a second voltage drop, said first voltage drop being measurable across the input drive lead terminal and the sense lead terminal and said second voltage drop being measurable across the sense lead terminal and the return drive lead terminal.

2. The reduced wire count voltage-drop sense system of claim 1 wherein the voltage drop across said light signal emitter is determinable by subtracting the second voltage drop from the first voltage drop.

3. The reduced wire count voltage-drop sense system of claim 1 wherein said light signal emitter comprises one of a light-emitting diode and a laser diode.

4. The reduced wire count voltage-drop sense system of claim 1 wherein said input drive lead and said return drive lead comprise equal length wires made of the same material and having equal diameters.

5. The reduced wire count voltage-drop sensing system of claim 4 wherein the wires comprising said input drive lead and said return drive lead are disposed within the same sheath.

6. A reduced wire count voltage-drop sense system for use in photoplethysmography comprising:
   a plurality of input drive leads, each said input drive lead extending between an associated separate one of a corresponding plurality of input drive lead terminals associated therewith and an associated separate one of a corresponding plurality of light signal emitter input terminals;
   a common return lead extending between a common light signal emitter output terminal and a common return lead terminal; and
   a sense lead extending between said common light signal emitter output terminal and a sense lead terminal;
   wherein a voltage drop across any one of a plurality of light signal emitters operable to illuminate a patient tissue site and connected between separate ones of said light signal emitter input terminals and said common light signal emitter output terminal when a drive current is applied therethrough via an associated one of said input drive leads is determinable from a first voltage drop and a second voltage drop, said first voltage drop being measurable across said input drive lead terminal associated with said input drive lead associated with said any one of said plurality of light signal emitters and said sense lead terminal, said second voltage drop being measurable across said sense lead terminal and said common return lead terminal.

7. The reduced wire count voltage-drop sense system of claim 6 wherein the voltage drop across said any one said plurality of light signal emitters is determinable by subtracting said second voltage drop from said first voltage drop.

8. The reduced wire count voltage-drop sense system of claim 6 wherein when current is simultaneously applied through more than one of said plurality of light signal emitters, the voltage drop across said any one of said plurality of light signal emitters is determinable by subtracting a portion of said second voltage drop from said first voltage drop.

9. The reduced wire count voltage-drop sense system of claim 6 wherein each said light signal emitter comprises one of a light-emitting diode and a laser diode.

10. The reduced wire count voltage-drop sense system of claim 6 wherein said input drive leads and said common return lead comprise equal length wires made of the same material.

11. The reduced wire count voltage-drop sensing system of claim 10 wherein the wires comprising said input drive leads and said common return lead are disposed within the same sheath.

12. The reduced wire count voltage-drop sense system of claim 10 wherein the wires comprising said input drive leads have equal cross-sectional areas and the wire comprising said common return lead has a cross-sectional area equal to the number of said input drive leads multiplied by the cross-sectional area of one of the wires comprising said input drive leads.

13. A reduced wire count photoplethysmographic probe comprising:
   a plurality of light signal emitters operable to illuminate a patient tissue site, each said light signal emitter having an input terminal and an output terminal, the output terminals of said light signal emitters being connected in common with one another;
   a plurality of input drive leads, each said input drive lead being associated with one of said light signal emitters and extending between an associated separate one of a corresponding plurality of input drive lead terminals and the input terminal of its associated light signal emitter;
   a common return drive lead extending between the commonly connected output terminals of the light signal emitters and a common return drive lead terminal; and
   a sense lead extending between the commonly connected output terminals of said light signal emitters and a sense lead terminal;
   wherein a voltage drop across any one said light signal emitters when it is turned on by applying a drive current therethrough via said input drive lead associated therewith is determinable from a first voltage drop and a second voltage drop, said first voltage drop being measurable across the input drive lead terminal associated with said input drive lead associated with said any one of said light signal emitters and the sense lead terminal, said second voltage drop being measurable across the sense lead terminal and the common return drive lead terminal.

14. The reduced wire count photoplethysmographic probe of claim 13 wherein the voltage drop across said any one said plurality of light signal emitters is determinable by subtracting the second voltage drop from the first voltage drop.

15. The reduced wire count photoplethysmographic probe of claim 14 wherein when more than one light signal emitter is simultaneously turned on, the voltage drop across said any one of said light signal emitters is determinable by subtracting a portion of the second voltage drop from the first voltage drop.

16. The reduced wire count photoplethysmographic probe of claim 13 wherein each said light signal emitter comprises one of a light-emitting diode and a laser diode.

17. The reduced wire count photoplethysmographic probe of claim 13 wherein said input drive leads and said common return drive lead comprise equal length wires made of the same material.

18. The reduced wire count photoplethysmographic probe of claim 17 wherein the wires comprising said input drive leads and said common return drive lead are disposed within the same sheath.

19. The reduced wire count photoplethysmographic probe of claim 17 wherein the wires comprising said input drive leads have equal cross-sectional areas and the wire comprising said common return drive lead has a cross-sectional area equal to the number of input drive leads multiplied by the cross-sectional area of one of the wires comprising said input drive leads.

20. A reduced wire count photoplethysmographic probe comprising:

at least two pairs of light signal emitters, each pair of light signal emitters being connected in a back-to-back relation with one another between an input terminal of said pair and an output terminal of said pair wherein one of the light signal emitters is forward biased and one is reverse biased when a voltage is applied across the input and output terminals of the pair, the output terminals of each pair of said light signal emitters being connected in common with one another;

a plurality of input drive leads, each said input drive lead being associated with one of said pairs of light signal emitters and extending between an associated separate one of a corresponding plurality of input drive lead terminals and the input terminal of its associated pair of light signal emitters;

a common return drive lead extending between the commonly connected output terminals of said pairs of light signal emitters and a common return drive lead terminal; and a sense lead extending between the commonly connected output terminals of said pairs of light signal emitters and a sense lead terminal;

wherein a voltage drop across any one of said pairs of light signal emitters when a drive current is applied therethrough via said input drive lead associated therewith is determinable from a first voltage drop and a second voltage drop, said first voltage drop being measurable across the input drive lead terminal associated with said input drive lead associated with said any one of said pairs of light signal emitters and the sense lead terminal, said second voltage drop being measurable across the sense lead terminal and the common return drive lead terminal.

21. The reduced wire count photoplethysmographic probe of claim 20 wherein the voltage drop across said any one said pairs of light signal emitters is determinable by subtracting the second voltage drop from the first voltage drop.

22. The reduced wire count photoplethysmographic probe of claim 21 wherein when more than one light signal emitter is simultaneously turned on, the voltage drop across said any one of said pairs of light signal emitters is determinable by subtracting a portion of the second voltage drop from the first voltage drop.

23. The reduced wire count photoplethysmographic probe of claim 20 wherein each said light signal emitter comprises one of a light-emitting diode and a laser diode.

24. The reduced wire count photoplethysmographic probe of claim 20 wherein said input drive leads and said common return drive lead comprise equal length wires made of the same material.

25. The reduced wire count photoplethysmographic probe of claim 24 wherein the wires comprising said input drive leads and said common return drive lead are disposed within the same sheath.

26. The reduced wire count photoplethysmographic probe of claim 24 wherein the wires comprising said input drive leads have equal cross-sectional areas and the wire comprising said common return drive lead has a cross-sectional area equal to the number of input drive leads multiplied by the cross-sectional area of one of the wires comprising said input drive leads.

27. A method of determining a desired voltage drop across any one of a plurality of light signal emitters operable to illuminate a patient tissue site and having separate input terminals and commonly connected output terminals, said method comprising:

measuring a first voltage drop across a sense lead terminal connected by a sense lead to the commonly connected output terminals of the light signal emitters and an input drive lead terminal connected by an input drive lead to the input terminal of the light signal emitter across which the desired voltage drop is to be determined when a drive current is supplied thereto via the input drive lead;

measuring a second voltage drop across the sense lead terminal and a common return drive lead terminal connected by a common return drive lead to the commonly connected output terminals of the light signal emitters; and utilizing the first voltage drop and the second voltage drop to determine the desired voltage drop.

28. The method of claim 27 wherein said step of utilizing comprises:

subtracting the second voltage drop from the first voltage drop to determine the desired voltage drop.

29. The method of claim 27 wherein when the common return drive lead has a different diameter than the input drive lead, said step of utilizing further comprises: multiplying the second voltage drop by a ratio of the cross-sectional area of the common return drive lead to the cross-sectional area of the input drive lead.

30. The method of claim 27 wherein when drive currents are simultaneously supplied to more than one of the plurality of light signal emitters, said step of utilizing comprises:

subtracting a portion of the second voltage drop from the first voltage drop to determine the desired voltage drop.

31. The method of claim 30 wherein said step of utilizing further comprises:

apportioning the second voltage drop in accordance with the level of each drive current that is supplied to the light signal emitters in order to obtain the portion of the second voltage drop that is subtracted from the first voltage drop in said subtracting step.

32. A method of determining a desired voltage drop across any one of a plurality of light signal emitters operable to illuminate a patient tissue site and having separate input terminals and commonly connected output terminals, said method comprising:

measuring a first voltage drop across a sense lead terminal connected by a sense lead to the commonly connected output terminals of the light signal emitters and ah input drive lead terminal connected by an input drive lead to the input terminal of the light signal emitter across which the desired voltage drop is to be determined when a drive current is supplied thereto via the input drive lead;

measuring a second voltage drop across the sense lead terminal and a common return drive lead terminal connected by a common return drive lead to the commonly connected output terminals of the light signal emitters; and utilizing the first voltage drop and the second voltage drop to determine the desired voltage drop, wherein said step of utilizing comprises subtracting the second voltage drop from the first voltage drop to determine the desired voltage drop, and wherein, when the common return drive lead has a different diameter than the input drive lead, said step of utilizing further comprises multiplying the second voltage drop by a ratio of the cross-sectional area of the common return drive lead to the cross-sectional area of the input drive lead prior to subtracting the second voltage drop from the first voltage drop.

33. The method of claim 32 wherein, in said step of utilizing, only a portion of the second voltage drop is subtracted from the first voltage drop to determine the desired voltage drop when drive currents are simultaneously supplied to more than one of the plurality of light signal emitters.

34. The method of claim 33 wherein said step of utilizing further comprises:

apportioning the second voltage drop in accordance with the level of each drive current that is supplied to the light signal emitters in order to obtain the portion of the second voltage drop that is subtracted from the first voltage drop in said utilizing step.

* * * * *